(12) United States Patent
Schneider

(10) Patent No.: US 12,144,376 B2
(45) Date of Patent: Nov. 19, 2024

(54) DRY CHAMBER LASER VAPORIZER

(71) Applicant: LUMENARY, INC., Petaluma, CA (US)

(72) Inventor: Robert Scott Schneider, Dillon Beach, CA (US)

(73) Assignee: LUMENARY, INC., Petaluma, CA (US)

( * ) Notice: Subject to any disclaimer, the term of this patent is extended or adjusted under 35 U.S.C. 154(b) by 842 days.

(21) Appl. No.: 17/156,103

(22) Filed: Jan. 22, 2021

(65) Prior Publication Data

US 2021/0137166 A1     May 13, 2021

Related U.S. Application Data

(63) Continuation of application No. 16/901,331, filed on Jun. 15, 2020, now Pat. No. 10,918,131.

(60) Provisional application No. 62/861,145, filed on Jun. 13, 2019.

(51) Int. Cl.
| | |
|---|---|
| *A24F 40/46* | (2020.01) |
| *A24F 40/20* | (2020.01) |
| *A24F 40/48* | (2020.01) |
| *A24F 40/50* | (2020.01) |
| *G02B 27/09* | (2006.01) |

(52) U.S. Cl.
CPC .............. *A24F 40/46* (2020.01); *A24F 40/20* (2020.01); *A24F 40/48* (2020.01); *A24F 40/50* (2020.01); *G02B 27/0916* (2013.01); *G02B 27/0955* (2013.01)

(58) Field of Classification Search
None
See application file for complete search history.

(56) References Cited

U.S. PATENT DOCUMENTS

| | | |
|---|---|---|
| 2006/0047368 A1 | 3/2006 | Maharajh et al. |
| 2017/0368637 A1 | 12/2017 | Giese et al. |
| 2019/0029318 A1 | 1/2019 | Schneider |
| 2019/0116883 A1 | 4/2019 | Rogan et al. |
| 2019/0142071 A1 | 5/2019 | Seok |

FOREIGN PATENT DOCUMENTS

WO      98/17130 A1     4/1998

OTHER PUBLICATIONS

International Search Report and Written Opinion issued for PCT/US2020/037725, mailed on Aug. 18, 2020.

*Primary Examiner* — Katherine A Will
(74) *Attorney, Agent, or Firm* — Perkins Coie LLP; Michael A. Glenn

(57) ABSTRACT

A laser heater assembly for a vaporizer includes a power source, a laser source, a lens, and a reaction chamber. The lens is disposed within the optical path. During operation, the laser source emits light, the light propagating along an optical path during operation of the light source. The lens receives the emitted light from the laser source, and outputs a modified light having an energy profile that is substantially spatially uniform. The modified light traverses at least a portion of an opening of the reaction chamber and vaporizes a vaporization substance (e.g., a dry plant material) received within the reaction chamber. The emitted light can be collimated light, and the modified light can be a homogeneous line profile beam.

9 Claims, 16 Drawing Sheets

DRY CHAMBER LASER VAPORIZER

CROSS-REFERENCE TO RELATED APPLICATIONS

This application is a continuation of U.S. patent application Ser. No. 16/901,331, filed Jun. 15, 2020, and claims the benefit of U.S. Provisional Patent Application No. 62/861,145, filed Jun. 13, 2019 and titled "Dry Chamber Laser Vaporizer," the entirety of each of which is incorporated herein in its entirety by this reference thereto.

FIELD

The present disclosure relates to vaporizer technology, and more specifically, to the heating of vaporizable materials.

BACKGROUND

Vaporizers are implements designed to vaporize one or more substances for inhalation by a user. Substances vaporized by vaporizers typically include plant-derived ingredients.

SUMMARY

In some embodiments, an apparatus (e.g., a laser heater assembly) includes a power source, a laser source (e.g., a laser diode), a lens, and a reaction chamber. The laser source (e.g., a laser diode) is electrically coupled to the power source and configured to emit light, the light propagating along an optical path during operation of the light source. The lens is disposed within the optical path. The reaction chamber is also disposed within the optical path, and includes an opening defined therein. The lens is configured to receive, during operation, emitted light from the laser source, and output a modified light having an energy profile that is substantially spatially uniform. The laser source and the lens are configured such that, during operation, the modified light traverses at least a portion of the opening of the reaction chamber and vaporizes a vaporization substance (e.g., a dry plant material, optionally ground to a predefined size and/or density) disposed within the reaction chamber. The light can be collimated light, and the modified light can be a homogeneous line profile beam. The lens can be a Powell lens configured to homogenize an energy field of the light. In some implementations, the laser source includes a Powell lens, and the light is collimated light.

In some embodiments, an apparatus (e.g., a vaporizer) includes a vapor tube including a mouthpiece, a power source (e.g., a laser diode), a laser source, a lens, and a reaction chamber. The laser source is electrically coupled to the power source and configured to emit light, the light propagating along an optical path during operation of the light source. The lens is disposed within the optical path. The reaction chamber is also disposed within the optical path, and has an opening (e.g., a rectangular or rounded rectangular opening) defined therein. The vapor tube is fluidly coupled to (or in fluid communication with) at least a portion of the reaction chamber. The lens is configured to receive, during operation, emitted light from the laser source, and output a modified light having an energy profile that is substantially spatially uniform. The laser source and the lens are configured such that, during operation, the modified light traverses at least a portion of the opening of the reaction chamber and vaporizes a vaporization substance (e.g., a dry plant material, optionally ground to a predefined size and/or density) disposed within the reaction chamber. The light can be collimated light and the modified light can be a homogeneous line profile beam. The lens can be a Powell lens configured to homogenize an energy field of the light. In some implementations, the laser source includes a Powell lens and the light is collimated light.

BRIEF DESCRIPTIONS OF THE DRAWINGS

DETAILED DESCRIPTION

Figure 1:
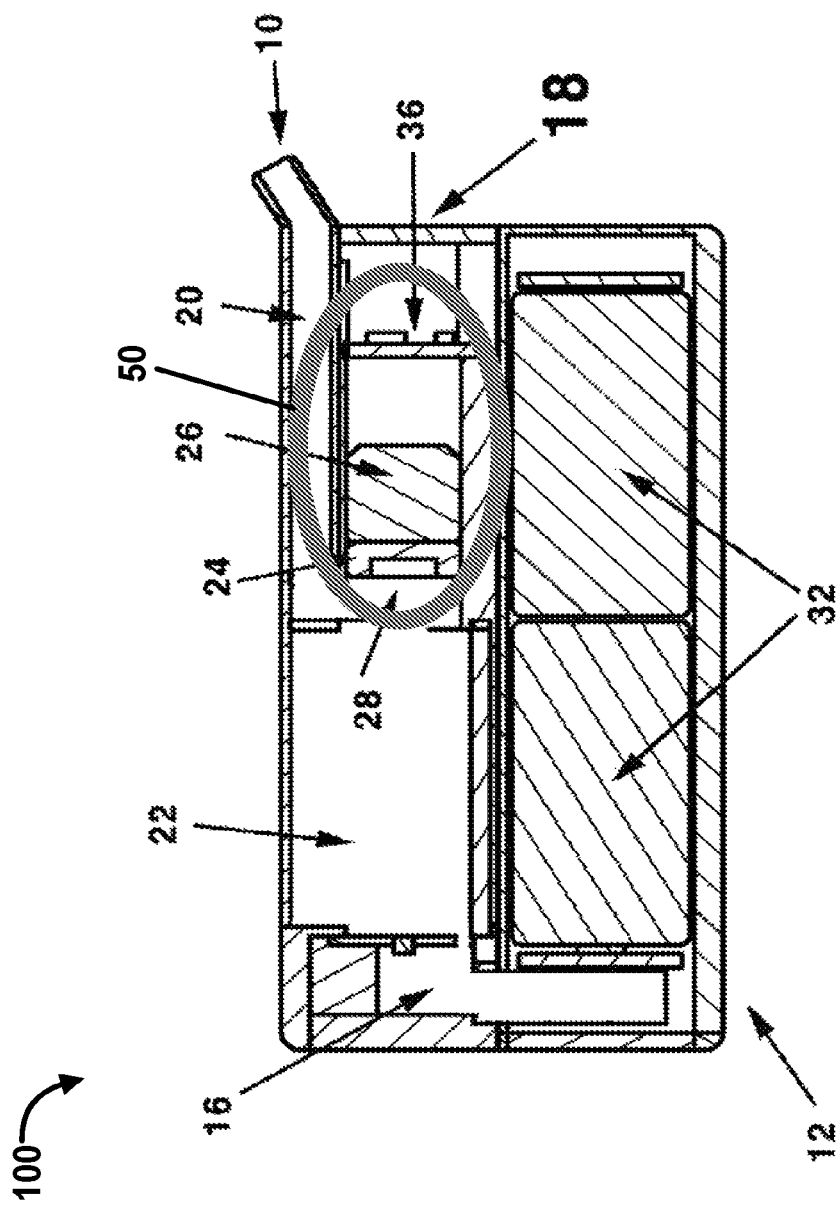
FIG. 1 is a diagram showing a laser-based vaporizer, according to some embodiments.

Known vaporizers often include heaters that, by virtue of their design, have relatively long heat-up times (particularly when the material to be vaporized is a dry material) and/or can cause heating of portions of the vaporizer other than the substance intended to be vaporized. For example, known vaporizer heaters can cause heating of the entire vaporization chamber of the vaporizer, potentially causing an undesirable temperature profile that causes an unpleasant taste of the vapor. Moreover, known vaporizer heaters can cause heating of the outer housing, mouthpiece and/or other external components of the vaporizer, potentially causing discomfort to a user.

Vaporizer embodiments of the present disclosure, by contrast, can achieve rapid and highly localized heating of vaporization substances, such that flavor profiles of the resulting vapors can be improved and more consistent than known methods, and/or the heating of external components of the vaporizer can be reduced or eliminated. The concentrated energy delivered by a laser beam, according to some embodiments, can achieve instantaneous, substantially instantaneous, or significantly faster heating of a vaporization substance (e.g., a dry material), as compared with known heaters that do not use a laser. Systems and methods set forth herein can be compatible with both dry vaporization substances and liquid vaporization substances. As used herein, dry vaporization substances, or "dry materials," can refer to organic materials such as plant materials (raw or processed), e.g., leaves, buds, flowers, and stems; or fungi. When the vaporization substance is a dry vaporization substance, the vaporization chamber of the vaporizer can be referred to as a "dry chamber." In some embodiments, vaporization of dry material such as flower or leaf is achieved using direct irradiation of the dry material, to produce a cannabinoid-containing vapor.

In some embodiments of the present disclosure, a vaporizer includes a laser-based heater (e.g., including one or more laser diodes) and is configured to emit, internally to the vaporizer, laser radiation (i.e., light) having a substantially homogeneous energy profile. For example, radiation from a laser diode, when initially emitted, can have a non-uniform (e.g., Gaussian) energy profile. The non-uniform laser radiation/light can be directed toward and caused to pass through one or more filters and/or lenses (e.g., a Powell lens), such that the energy profile of light exiting the one or more filters and/or lenses is substantially uniform (e.g., homogeneous in value) across a spot size thereof. For example, a Powell lens can convert a laser beam into a light beam having a substantially uniform energy profile, and a straight line shape. As used herein, a "substantially uniform" energy profile produced by a Powell lens is an energy profile having an intensity that is spatially uniform (e.g., +/−25%) across the entire length of the laser line that is generated, as contrasted with Gaussian beam profiles (having hot-spot center points and fading edges) generated by cylindrical lenses. The laser radiation can be directed at, and interact with, the vaporization substance directly and substantially without heating the air within the vaporizer (e.g., the air adjacent to the vaporization substance). The laser radiation can be generated without a ramp-up in temperature.

In some implementations, the vaporizer also includes an agitator or a mechanical tool (e.g., fin, blade, or spatula) that, during operation of the vaporizer, moves, displaces, shakes or otherwise mechanically disrupts the vaporization substance (e.g., a dry vaporization substance) such that as the homogeneous light interacts with the vaporization substance, new surfaces of the vaporization substance are placed within the path of the homogeneous light and "fresh" material is continually being vaporized. The mechanical disruption can be initiated via actuation of a power switch (e.g., upon interaction of a user with a power button, or automatically in response to a detected change in pressure upon suction on the mouthpiece by the user), and can be performed at a predetermined rate and/or speed. The rate and/or speed may be set, for example, by a microprocessor on board the vaporizer, and is optionally modifiable by the user (e.g., via direct interaction with the vaporizer and/or via wireless communication between a software application of a mobile device of the user and the microprocessor).

FIG. 1 is a diagram showing a handheld laser-based vaporizer, in an example configuration, according to some embodiments. As shown in FIG. 1, the vaporizer 100 includes a main housing 12, a mouthpiece 10 in fluid communication with a vapor tube 20 and a vaporization chamber 22, a power switch 18 electrically coupled to one or more power sources 32 (e.g., batteries, such as lithium ion batteries and/or rechargeable power sources) and electrically coupled to an optional power regulator 36, one or more laser diodes 24 in thermal contact with a heat sink 26, and a reaction chamber 16. During operation, a laser beam generated by the one or more laser diodes 24 is directed, via a focusing lens 28, toward the reaction chamber 16. The focusing lens 28, the heat sink 26, the power regulator 36, and/or any mechanical actuators or other components (not shown), collectively, can be referred to as a laser heater assembly 50. Although not shown in FIG. 1, the vaporizer 100 can include one or more interlocks to prevent inadvertent exposure of a user to the laser beam/radiation of the one or more laser diodes. Some or all components of the vaporizer 100 can be modular (e.g., removable and/or replaceable). Additional details about vaporizer construction and operation can be found, by way of example only, in U.S. Patent Application Publication No. 2019/0029318, titled "Handheld Apparatus for Vaporization of Plant-Based on Synthetic Compounds by Laser," the entire contents of which are herein incorporated by reference in their entirety.

In some embodiments, the main housing 12 is made of a metal, such as aluminum, and includes a viewport cover. The viewport cover can be slidable along a direction toward the mouthpiece into an open position, to reveal the reaction chamber. The contents of the reaction chamber can be viewable through a light spectrum specific, safety plastic or glass viewport that is balanced (e.g., is sufficiently opaque, tinted, or otherwise light-blocking, for example by virtue of a coating applied thereon) to block dangerous light radiation emissions, but transparent enough for a user to safely view the reaction taking place within the reaction chamber (e.g., the cartridge) during operation.

Figure 2B:
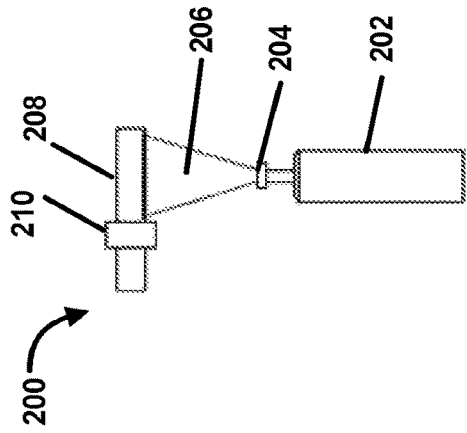
FIGS. 2A-2D are diagrams showing a laser heater assembly for a vaporizer, the laser heater assembly configured to use radiant heat and convected air for vaporization of a vaporization substance, according to some embodiments.
Figure 2D:
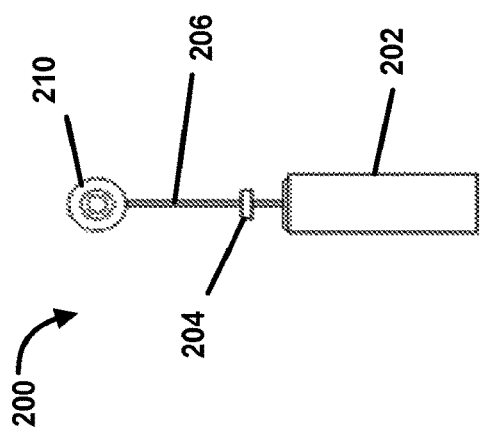
Figure 2A:
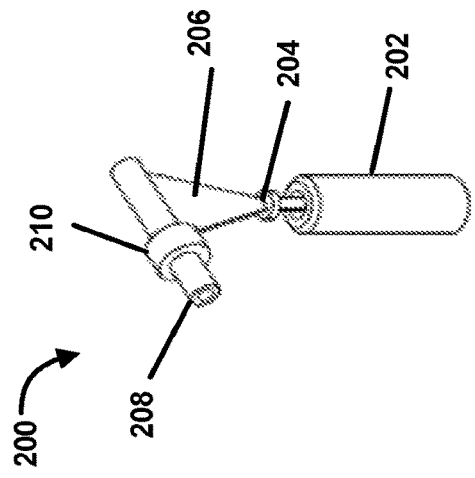
Figure 2C:
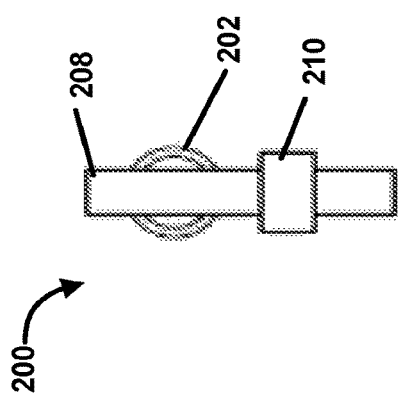

FIGS. 2A-2D are diagrams showing a laser heater assembly for a vaporizer, some or all components of which are compatible for use as the laser heater assembly 50 of vaporizer 100 of FIG. 1, according to some embodiments. Specifically, FIG. 2A shows a rear view, FIG. 2B shows a perspective view, FIG. 2C shows atop view, and FIG. 2D shows a side view of the laser heater assembly 200. The laser heating vaporizer configuration 200 uses radiant heated convected air to achieve vaporization of a vaporization substance. As shown in FIGS. 2A-2D, a laser source 202 is optically aligned with a Powell lens 204 and is configured, during use, to emit light 206 toward an air chamber 208 that is in fluid communication with a vaporization chamber 210 containing a vaporization material. Light emitted from the Powell pens 204 impinges the outer surface of the air chamber 208 that is also in contact with air (e.g., ambient air and/or forced air). In some implementations, during operation of the laser source 202, the wall of the air chamber 208 becomes heated by the impinging light, and the air is turn heated by the heat radiating from the heated chamber wall. The heated air within the air chamber 208 can then be forced (e.g., via suction applied by a user via a mouthpiece of the vaporizer) into the vaporization chamber 210 containing the vaporization substance to cause vaporization of the vaporization substance. Alternatively or in addition, during operation of the laser source 202, the wall of the air chamber 208 becomes heated by the impinging light, and the heat within the chamber wall is transferred, via thermal conduction, to the vaporization chamber where the heat emanates through the vaporization substance and/or around the vaporization substance via a highly insulated vaporization chamber wall. The highly insulated vaporization chamber wall can be made of or include, by way of non-limiting example, one or more of: an aerogel, an aerogel alloy, fiberglass, ceramic, etc.

Figure 3A:
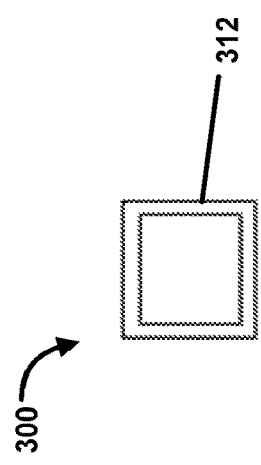
FIGS. 3A-3D are diagrams showing a laser heater assembly for a vaporizer, the laser heater assembly including a Powell lens for generating a substantially uniform line profile beam for vaporization of a vaporization substance, according to some embodiments.
Figure 3B:
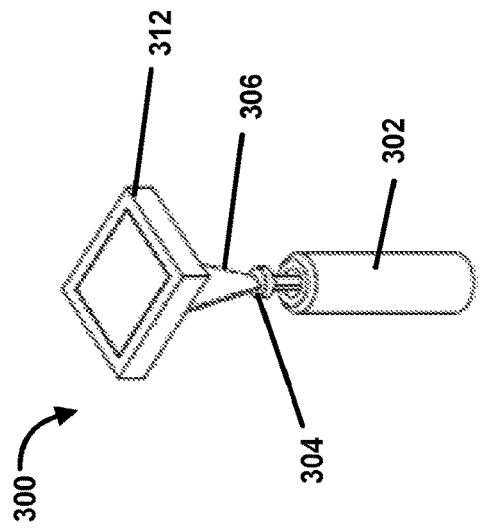
Figure 3C:
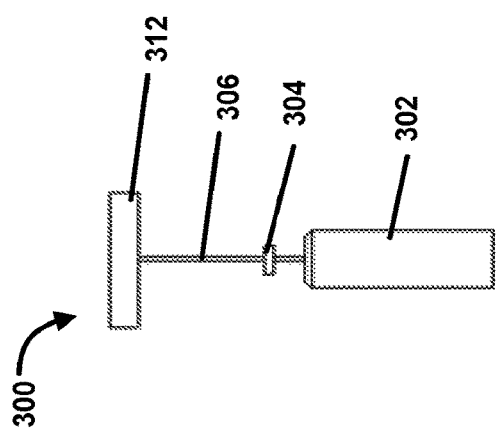
Figure 3D:
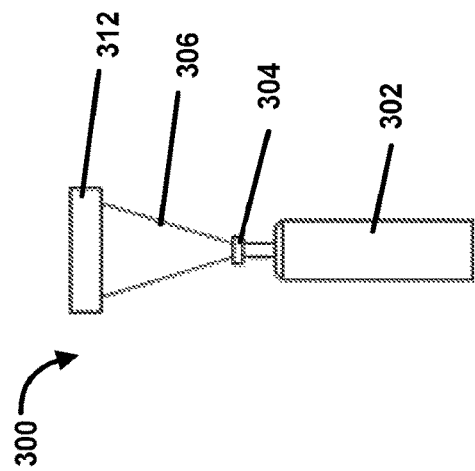

FIGS. 3A-3D are diagrams showing a laser heater assembly for a vaporizer, some or all components of which are compatible for use as the laser heater assembly 50 of vaporizer 100 of FIG. 1, according to some embodiments. Specifically, FIG. 3A shows a rear view, FIG. 3B shows a perspective view, FIG. 3C shows atop view, and FIG. 3D shows a side view of the laser heater assembly 300. As shown in FIGS. 3A-3D, a laser source 302 is optically aligned with a Powell lens 304 and is configured, during use, to emit light 306 toward a vaporization chamber 312 that contains a vaporization substance. The laser heating vaporizer configuration 300 uses the Powell lens 304 to convert a nominally collimated beam (i.e., between the laser source 302 and the Powell lens 304) into a substantially uniform (e.g., homogeneous) line profile beam 306. During operation, the line profile beam scans a vaporization substance, for example using an oscillating motorized mirror and/or by moving the vaporization substance and/or the vaporization chamber, to heat the vaporization substance to a temperature sufficient to cause vaporization of the vaporization substance. As noted above, the vaporizer (and, optionally, the laser heater assembly 300 itself) can include an agitator or a mechanical tool (e.g., fin, blade, or spatula) that, during operation of the vaporizer, moves, displaces, shakes or otherwise mechanically disrupts the vaporization substance (e.g., a dry vaporization substance) such that as the substantially uniform line profile beam 306 interacts with the vaporization substance, new surfaces of the vaporization substance are placed within the path of the substantially uniform line profile beam 306 and "fresh" material is continually being vaporized. As used herein, the phrase "nominally collimated" can refer to a beam of light or other electromagnetic radiation that includes substantially parallel rays, for example at least within a vicinity of a focal point or "waist" of the beam profile.

Figure 4B:
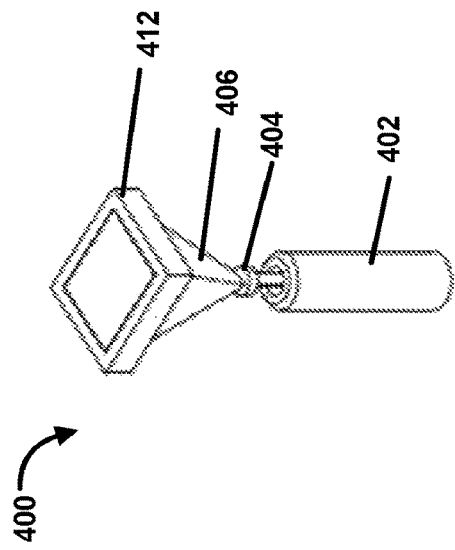
FIGS. 4A-4D are diagrams showing a laser heater assembly for a vaporizer, the laser heater assembly including one or more lenses to convert a nominally collimated beam into a substantially uniformly shaped beam for vaporization of a vaporization substance, according to some embodiments.
Figure 4D:
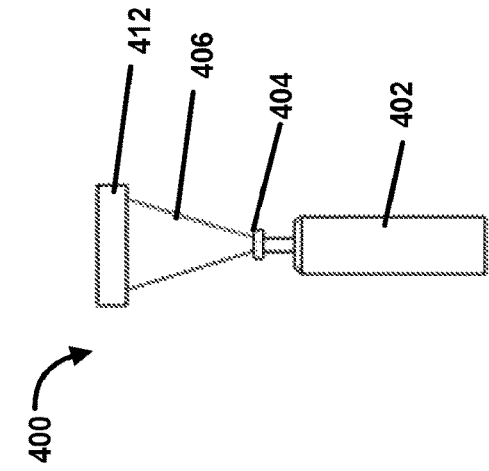
Figure 4A:
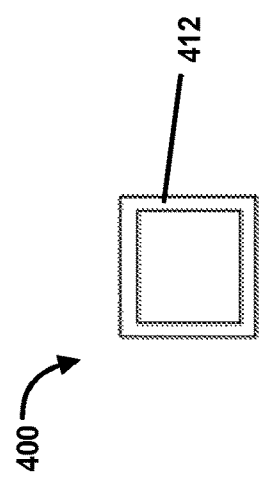
Figure 4C:
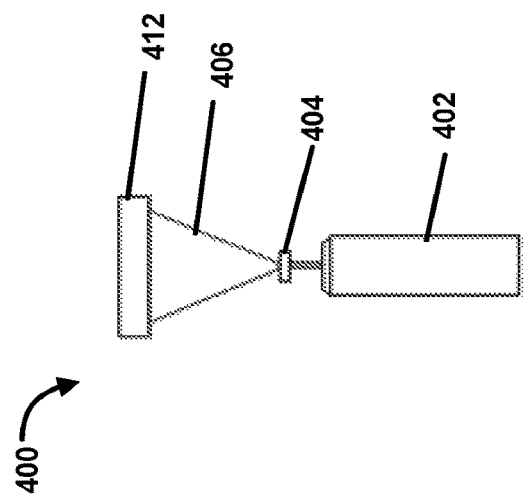

FIGS. 4A-4D are diagrams showing a laser heater assembly for a vaporizer, some or all components of which are compatible for use as the laser heater assembly 50 of vaporizer 100 of FIG. 1, according to some embodiments. Specifically, FIG. 4A shows a rear view, FIG. 4B shows a perspective view, FIG. 4C shows a top view, and FIG. 4D shows a side view of the laser heater assembly 400. As shown in FIGS. 4A-4D, a laser source 402 is optically aligned with one or more lenses 404 (e.g., an engineered diffuser lens, a micro lens array, etc.) and is configured, during use, to emit light 406 toward a vaporization chamber 412 that contains a vaporization substance. The laser heating vaporizer configuration 400 uses the one or more lenses 404 to convert a nominally collimated beam (i.e., between the laser source 402 and the one or more lenses 404) into a substantially uniformly shaped beam 406. During operation, the uniformly shaped beam 406 is directed toward (and, optionally, scanned across the surface of) a vaporization substance, for example using an oscillating motorized mirror and/or by moving the vaporization substance and/or the vaporization chamber 412, to achieve localized heating and vaporization of the vaporization substance. As noted above, the vaporizer (and, optionally, the laser heater assembly 400 itself) can include an agitator or a mechanical tool (e.g., fin, blade, or spatula) that, during operation of the vaporizer, moves, displaces, shakes or otherwise mechanically disrupts the vaporization substance (e.g., a dry vaporization substance) such that as the substantially uniformly shaped light beam 406 interacts with the vaporization substance, new surfaces of the vaporization substance are placed within the path of the substantially uniformly shaped light beam 406 and "fresh" material is continually being vaporized.

Figure 5B:
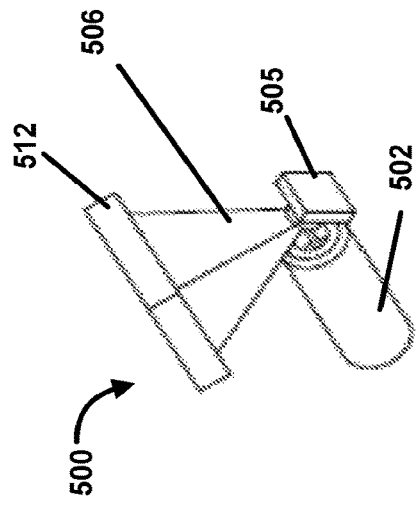
FIGS. 5A-5D are diagrams showing a laser heater assembly for a vaporizer, the laser heater assembly including mirror galvanometers that convert collimated laser light into a substantially uniform shaped light beam, for vaporization of a vaporization substance, according to some embodiments.
Figure 5D:
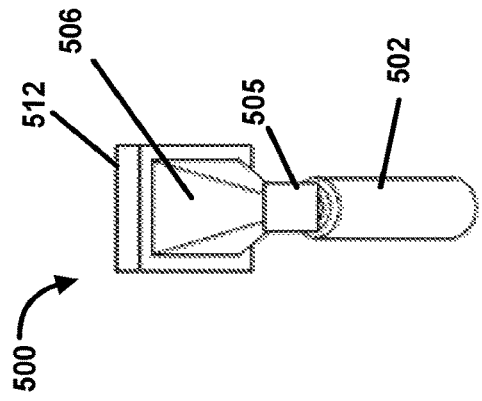
Figure 5A:
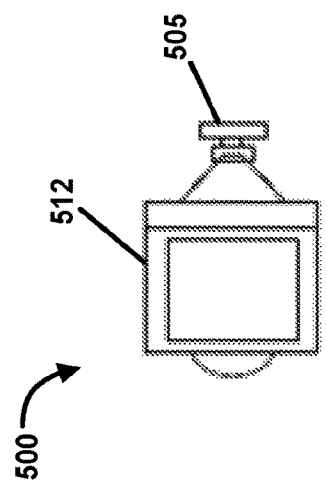
Figure 5C:
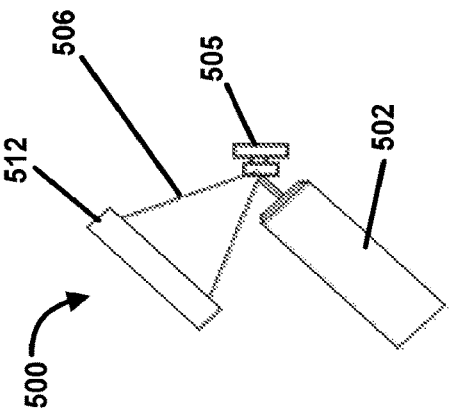

FIGS. 5A-5D are diagrams showing a laser heater assembly for a vaporizer, some or all components of which are compatible for use as the laser heater assembly 50 of vaporizer 100 of FIG. 1, according to some embodiments. Specifically, FIG. 5A shows a rear view, FIG. 5B shows a perspective view, FIG. 5C shows a top view, and FIG. 5D shows a side view of the laser heater assembly 500. As shown in FIGS. 5A-5D, a laser source 502 is optically coupled to one or more mirror galvanometers 505 that, during operation, receives and reflects a nominally collimated laser beam emitted from the laser source 502, the reflected beam 506 having a precisely formed uniform shape. A mirror galvanometer is an electromechanical instrument that deflects a light beam with a mirror in response to detecting an electric current. The reflected beam 506 travels toward a vaporization chamber 512 that contains a vaporization substance, and interacts with the vaporization substance to heat it to a temperature sufficient to cause it to vaporize. As noted above, the vaporizer (and, optionally, the laser heater assembly 500 itself) can include an agitator or a mechanical tool (e.g., fin, blade, or spatula) that, during operation of the vaporizer, moves, displaces, shakes or otherwise mechanically disrupts the vaporization substance (e.g., a dry vaporization substance) such that as the precisely formed uniform reflected light beam 506 interacts with the vaporization substance, new surfaces of the vaporization substance are placed within the path of the uniform light beam 506 and "fresh" material is continually being vaporized.

Figure 6B:
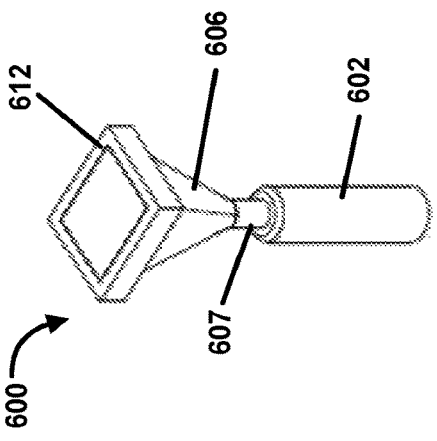
FIGS. 6A-6D are diagrams showing a laser heater assembly for a vaporizer, the laser heater assembly including a fiber optic array to convert a laser light beam into a substantially uniformly shaped light beam, for vaporization of a vaporization substance, according to some embodiments.
Figure 6D:
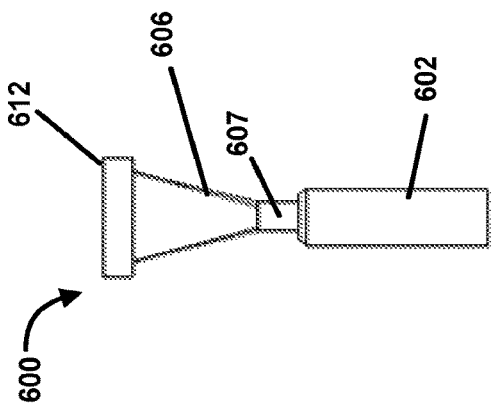
Figure 6A:
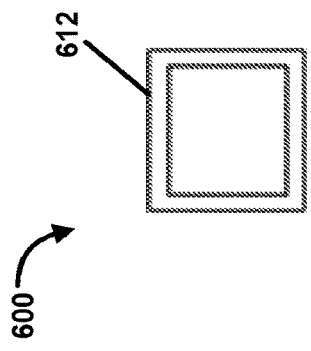
Figure 6C:
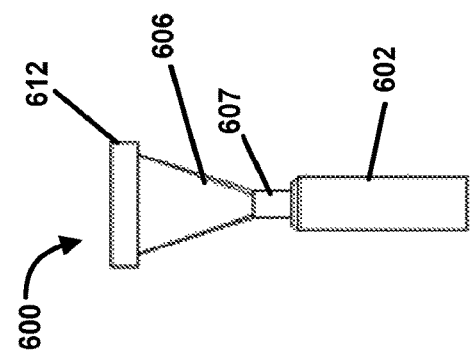

FIGS. 6A-6D are diagrams showing a laser heater assembly for a vaporizer, some or all components of which are compatible for use as the laser heater assembly 50 of vaporizer 100 of FIG. 1, according to some embodiments. Specifically, FIG. 6A shows a rear view, FIG. 6B shows a perspective view, FIG. 6C shows a top view, and FIG. 6D shows a side view of the laser heater assembly 600. As shown in FIGS. 6A-6D, a laser source 602 is optically coupled to a fiber optic array 607 configured, during operation, to convert a laser light beam emitted from the laser source 602 and received at the fiber optic array, into a substantially uniformly shaped light beam 606. The substantially uniformly shaped light beam 606 is directed toward a vaporization chamber 612 that contains a vaporization substance, and interacts with the vaporization substance to heat it to a temperature sufficient to cause it to vaporize. The fiber optic array 607 can include, for example, a regular linear or two-dimensional pattern of multiple fiber optic elements (e.g., multimode fibers). The vaporizer (and, optionally, the laser heater assembly 500 itself) can include an agitator or a mechanical tool (e.g., fin, blade, or spatula) that, during operation of the vaporizer, moves, displaces, shakes or otherwise mechanically disrupts the vaporization substance (e.g., a dry vaporization substance) such that as the substantially uniformly shaped light beam 606 interacts with the vaporization substance, new surfaces of the vaporization substance are placed within the path of the substantially uniformly shaped light beam 606 and "fresh" material is continually being vaporized. Alternatively or in addition, the fiber optic array 607 can be actuated during operation (e.g., shifted along one or more linear axes, rotated, etc.) to cause new surfaces of the vaporization substance to be placed within the path of the substantially uniformly shaped light beam 606.

Figure 7B:
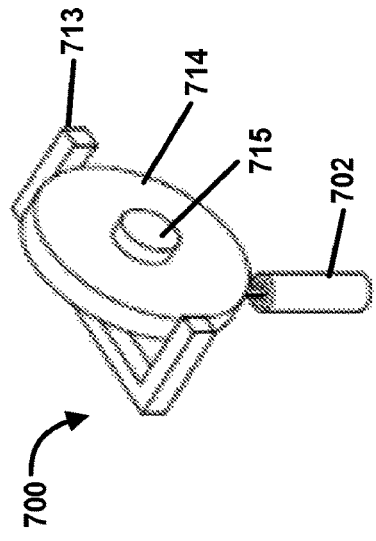
FIGS. 7A-7D are diagrams showing a laser heater assembly for a vaporizer, the laser heater assembly including an optical diverter that redirects a laser beam toward a target disc for vaporization of a vaporization substance, according to some embodiments.
Figure 7D:
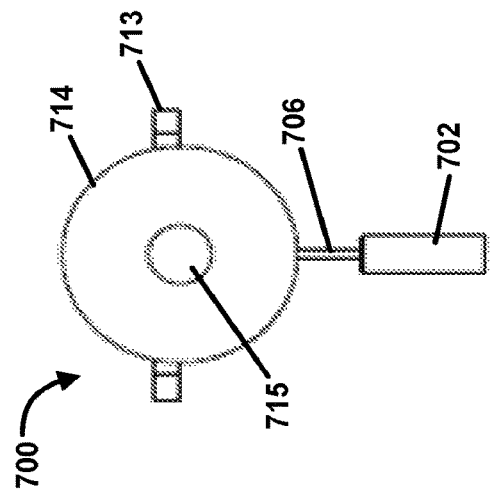
Figure 7A:
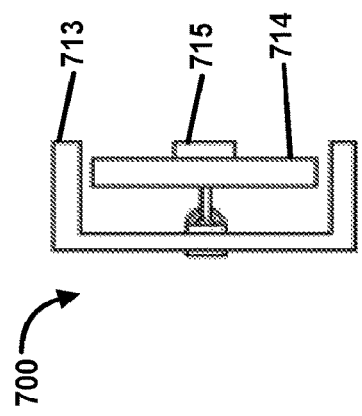
Figure 7C:
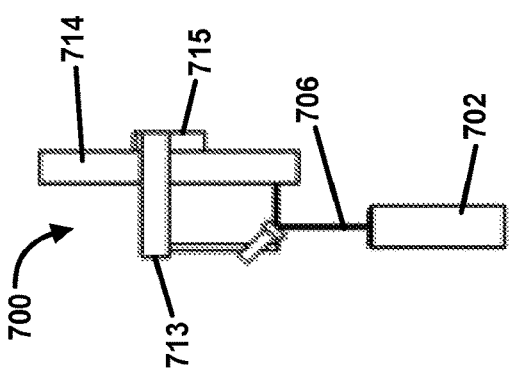

FIGS. 7A-7D are diagrams showing a laser heater assembly for a vaporizer, some or all components of which are compatible for use as the laser heater assembly 50 of vaporizer 100 of FIG. 1, according to some embodiments. Specifically, FIG. 7A shows a rear view, FIG. 7B shows a perspective view, FIG. 7C shows a top view, and FIG. 7D shows a side view of the laser heating vaporizer configuration 700. As shown in FIGS. 7A-7D, a laser source 702 is optically aligned with an optical diverter (e.g., a mirror) that, during operation, diverts a nominally collimated light beam 706, emitted from the laser source 702 and received at the optical diverter, such that a direction of travel of the light beam is modified (e.g., by about 90 degrees, as shown in FIG. 7C). The diverted light, during operation, is aimed at, travels toward, and impinges on a target disc 714 comprising or containing a vaporization substance. The target disc 714 is mounted to a frame 713 via a hub 715 about which the target disc 714 rotates or "spins" during operation. The rotation or spinning of the target disc 714 can be driven by a motor. The light beam 706 reaching the target disc 714 can be moved (e.g., rastered or scanned) from a center of the disc outward (i.e., radially, optionally back-and-forth) while the target disc rotates/spins, to cause a substantially uniform application of light energy (and, correspondingly, heat/thermal energy) to the target disc 714 and, as a consequence, to the vaporization substance of the target disc 714. In some implementations, a speed of the movement of the light beam 706 can be synchronized or substantially synchronized with a concurrent rotational speed of the target disc 714, for example based on a microcontroller of the vaporizer. Alternatively or in addition, the speed of the movement of the light beam 706 can vary based on a position on the rotating/spinning target disc 714 with which the light beam 706 is interacting at a given moment in time (e.g., speeding up as the light beam 706 nears a center region of the target disc 714 and slowing down as the light beam 706 nears an edge/perimeter region of the target disc 714), for example based on a microcontroller of the vaporizer. Although the target disc 714 is described above as rotating/spinning during operation, in other implementations the target disc 714 can remain stationary during operation (e.g., such that only the light beam 706 is moved during the generation of vapor (i.e., vaporization)).

Figure 8:
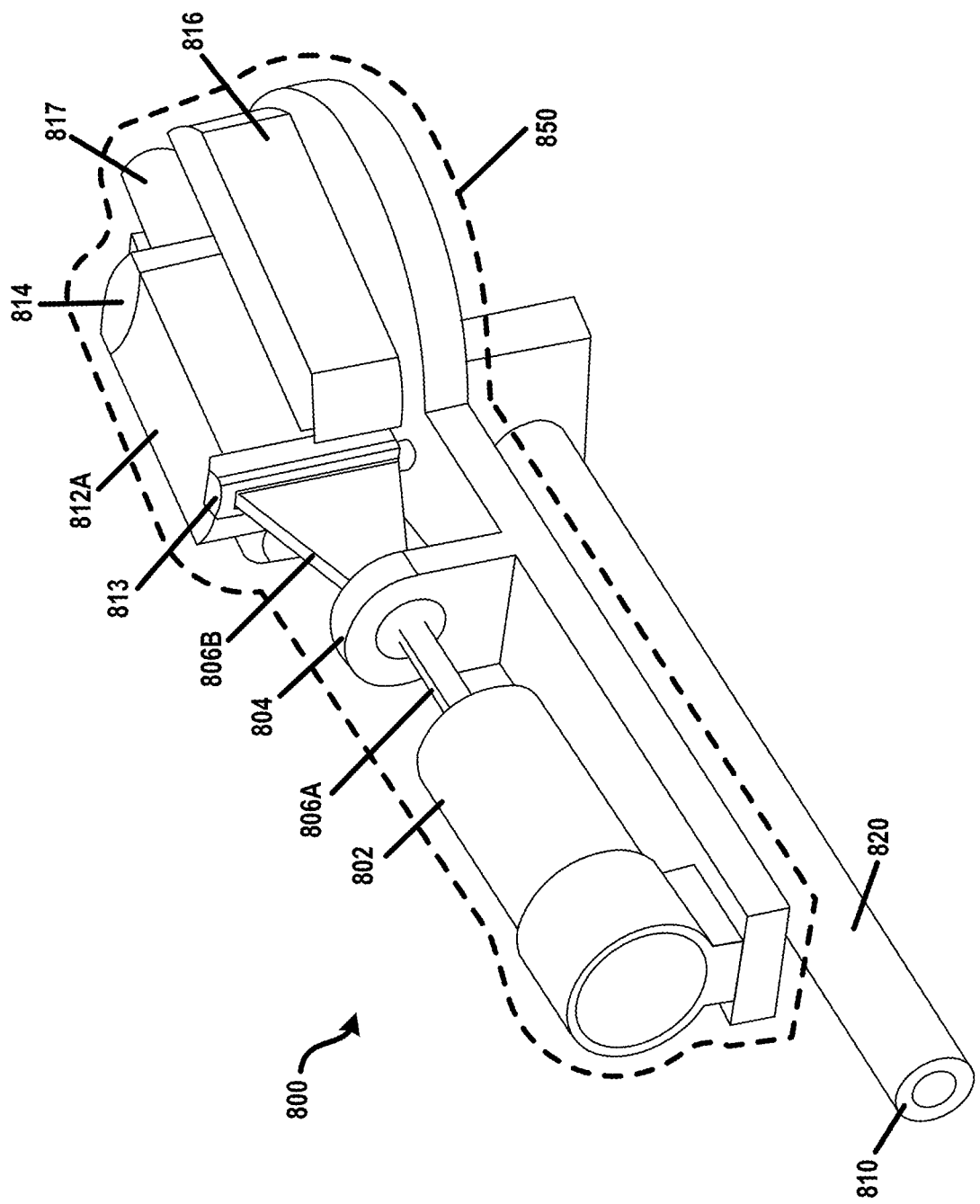
FIG. 8 is a diagram showing internal components of a vaporizer having a laser heater assembly and a motorized swivel reaction chamber, according to some embodiments.

FIG. 8 is a diagram showing internal components of a vaporizer 800, having a laser heater assembly and a motorized swivel reaction chamber (or "vaporization chamber"), according to some embodiments. As shown in FIG. 8, the vaporizer 800 includes a mouthpiece 810, a vapor tube 820, a laser source 802, one or more lenses 804, a reaction chamber 812A, at least one receptacle 816 for vaporized material, one or more motors (or other types of drives or actuators) 817. The reaction chamber 812A includes, or is attached to, a motorized mechanical agitator or scraper 813 and a plunger 814. The laser source 802 is optically aligned with the one or more lenses 804 (e.g., a collimator lens, a Powell lens, an engineered diffuser lens, a micro lens array, etc.) and is configured, during use, to emit light toward the reaction chamber 812A, to cause vaporization of at least a portion of a vaporization substance (not shown) disposed within the reaction chamber 812A. The vaporization substance can include a dry material. The motorized mechanical agitator or scraper 813 is configured, during operation of the vaporizer 800, to move portions of the vaporization substance that have been at least partially vaporized into the at least one receptacle 816. The plunger 814 is configured, during operation of the vaporizer 800, to move portions of the vaporization substance that have not yet been vaporized (i.e., "fresh" material from the vaporization substance) into a "target zone" of the reaction chamber 812A, for vaporization by light from the laser source 802. One or both of the motorized mechanical agitator or scraper 813 and the plunger 814 can be moved/actuated, during operation, by the one or motors 817 (e.g., each can be controlled by a common, single motor 817, each can be controlled by a separate motor from a pair of motors 817, etc.). A subset of the components of the vaporizer 800 of FIG. 8 can be collectively referred to as a laser heater assembly 850 (e.g., one or more of the laser source 802, the one or more lenses 804, the reaction chamber 812A, the at least one receptacle 816, the motor 817, the agitator/scraper 813, and the plunger 814). The vaporizer 800 optionally also includes a swivel motor (not shown), discussed below. In some embodiments, the vaporizer 800 also includes one or more onboard power sources (e.g., batteries, such as lithium ion batteries and/or rechargeable power sources), not shown, that are electrically coupled to, and configured during operation to supply power to, one or more of the laser source 802, the one or more lenses 804, the swivel motor, or the agitator/scraper 813. Alternatively or in addition, the vaporizer 800 is configured to receive power by being plugged into an external power source/supply. In other words, the vaporizer 800 can include a power cable for connection to the external power source (e.g., a wall output). Whether the power supply is an onboard battery or other source, or an external supply such as a wall output, the vaporizer 800 can be configured to deliver (e.g., via electrical connections) power from the power supply to one or more of the In some embodiments, during operation of the vaporizer 800, light initially emitted from the laser source 802 (light 806A) and arriving at the one or more lenses 804 is collimated light (e.g., by virtue of a collimator lens (not shown) that is integral to or adjacent to the laser source 802). The one or more lenses 804 includes a Powell lens, and the light exiting the Powell lens (light 806B) can be a homogeneous line profile beam. In other words, the Powell lens homogenizes the energy field of the light 806A, passing therethrough, into a line (e.g., a vertical line, as shown in FIG. 8). Alternatively or in addition, during operation of the vaporizer 800, the reaction chamber 812A, the agitator/scraper 813, the plunger 814, the one or motors 817 and the at least one receptacle 816 (collectively, a reaction chamber assembly) are collectively positioned on a motorized swivel that is configured to move in a back-and-forth motion (i.e., translate, alternately in opposing directions, along a linear path, such as a curved path), or to move in a rotational manner (i.e., at least partially move, alternately in opposing directions, about a rotational axis) atop a platform "P," such that a portion of a vaporization substance received within the reaction chamber 812A is slowly moved into a target zone of the reaction chamber 812A for vaporization by the light 806B (compare, e.g., FIGS. 9-11). The vaporization substance can be or include a dry material (e.g., a ground plant material). The portion of the vaporization substance can be a top layer of, or a portion of a top layer of, the vaporization substance. When the portion of the vaporization substance has been sufficiently vaporized (and, optionally, after the vaporized portion of the vaporization substance has been inhaled by a user, via the vapor tube 820 and the mouthpiece 810), residual material from the portion of the vaporization substance (e.g., "spent" material/waste) can be scraped, by the mechanical agitator/scraper 813 of the reaction chamber 812A and/or by virtue of the swivel motion, into a receptacle 816 of the vaporizer 800, such that a new portion of the vaporization substance is exposed and can be moved into the target zone for subsequent vaporization.

In some embodiments, one or more parameters such as a swivel rate, a swivel speed, a swivel pattern, a swivel timing, a dwell time for a given swivel position, an agitator/scraper rate, an agitator/scraper speed, an agitator/scraper timing, and/or an agitator/scraper pattern may be set, for example, by a microprocessor (not shown) on board the vaporizer 800. The one or more parameters can optionally be modifiable by a user (e.g., via direct interaction with one or more user interfaces (e.g., buttons, sliders, graphical user interfaces (GUIs) displayed thereon, etc.) of the vaporizer 800 and/or via wireless communication between the microprocessor of the vaporizer 800 and a software application ("app") of a mobile device of the user. Wireless communication can be performed, for example, via a transceiver of the vaporizer 800, via a wireless communications network.

Figure 9:
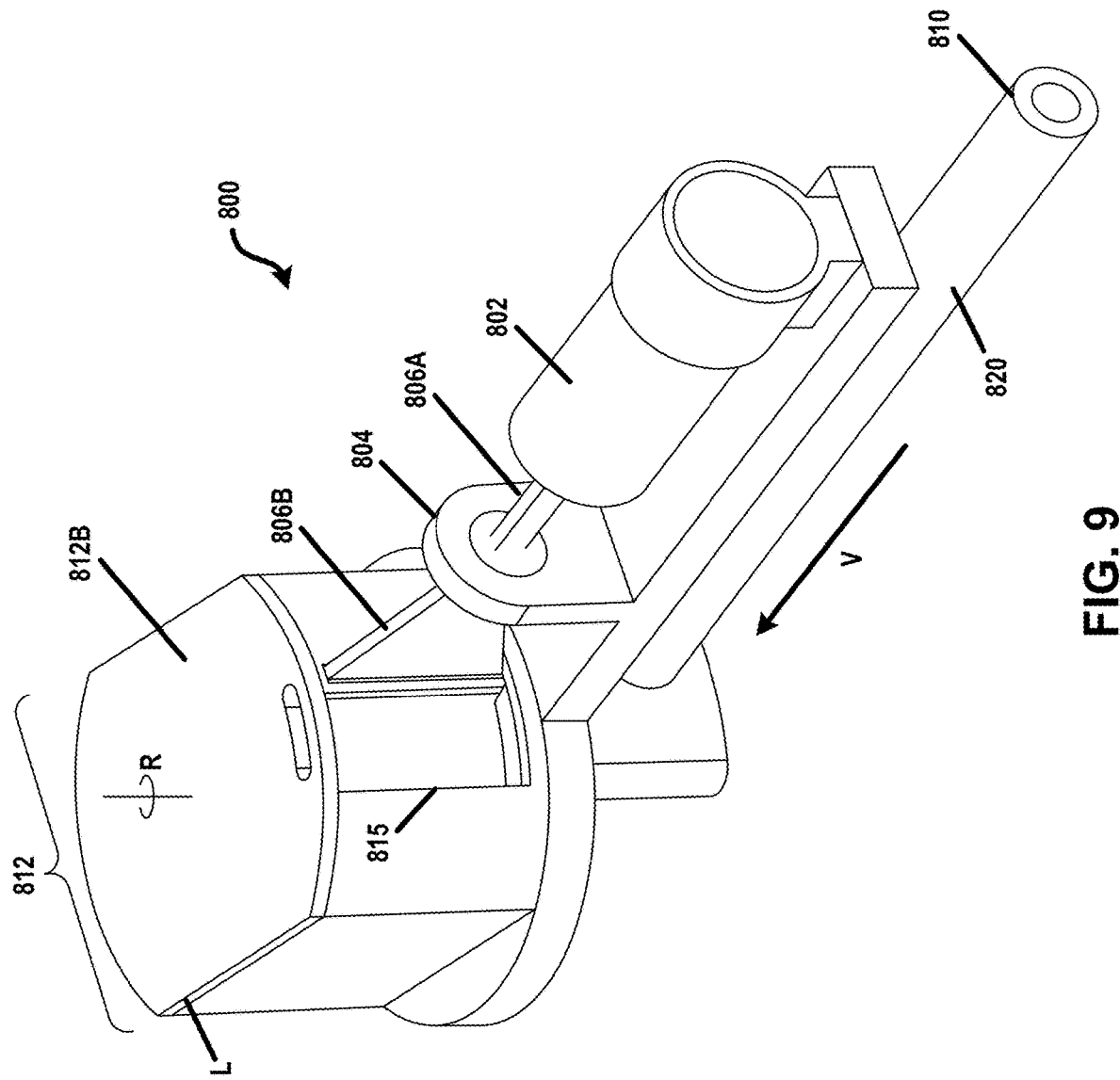
FIGS. 9-11 are diagrams showing the vaporizer of FIG. 8, fully assembled and with the reaction chamber at different raster positions.
Figure 10:
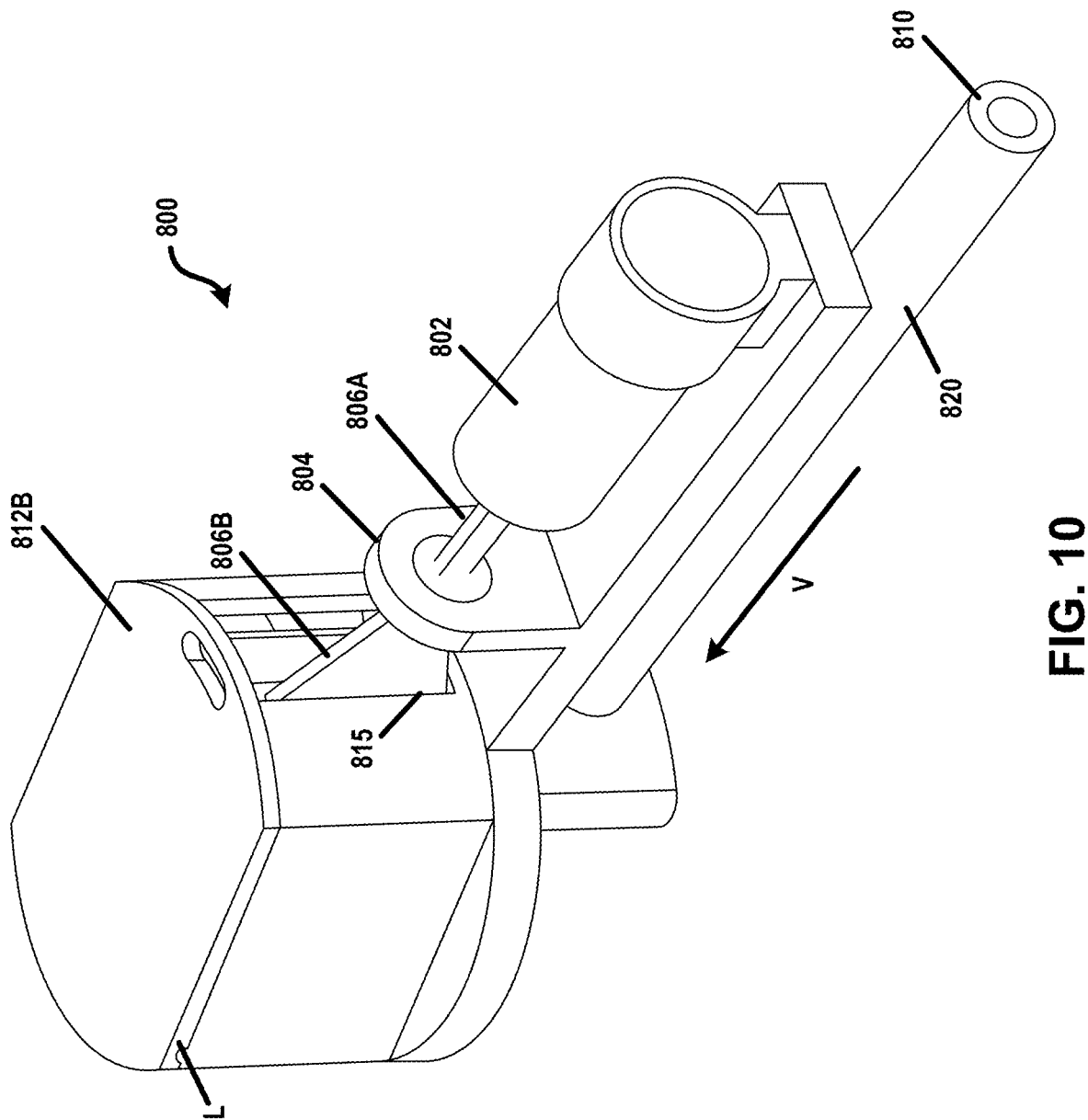
Figure 11:
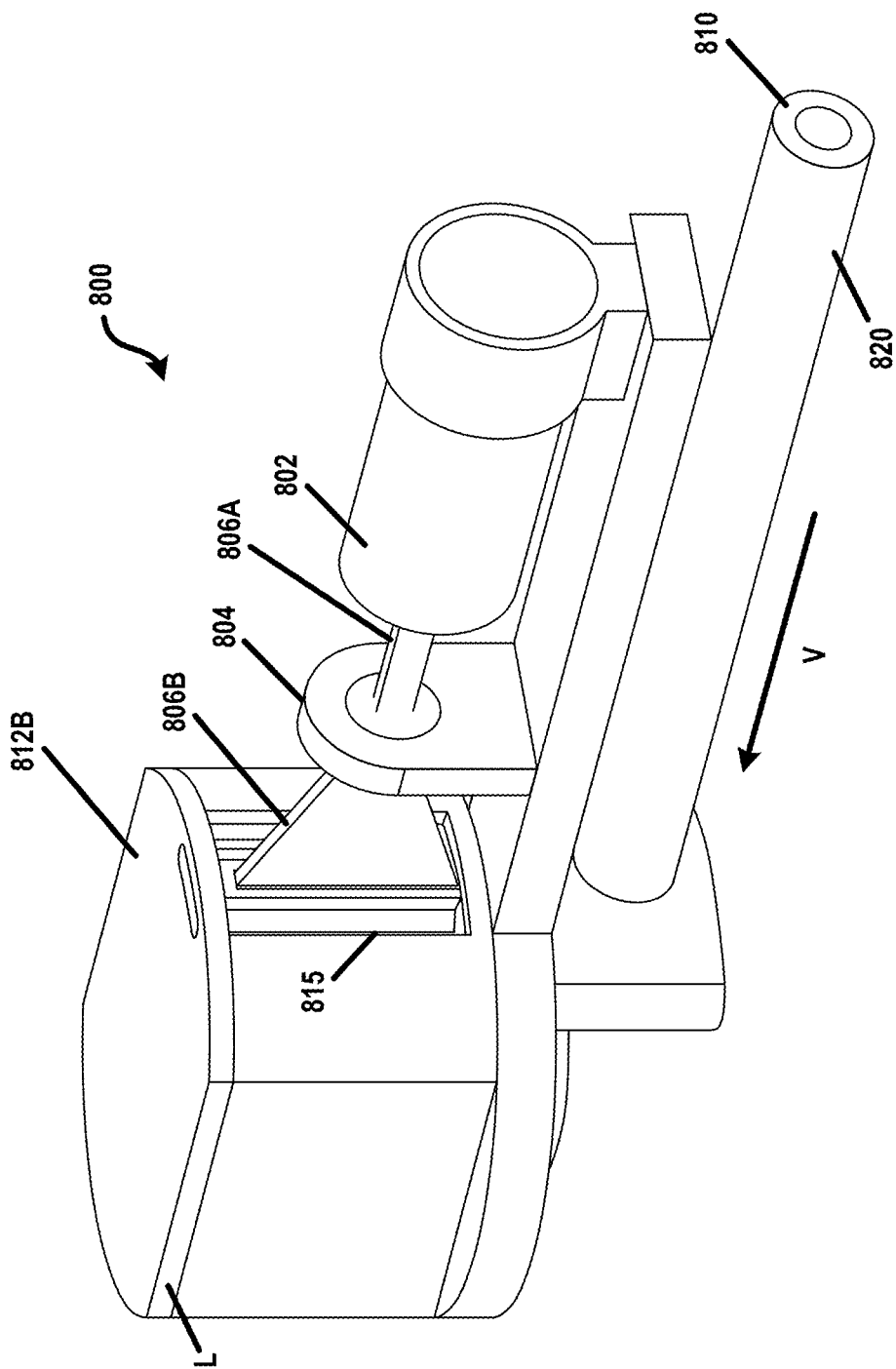
Figure 12A:
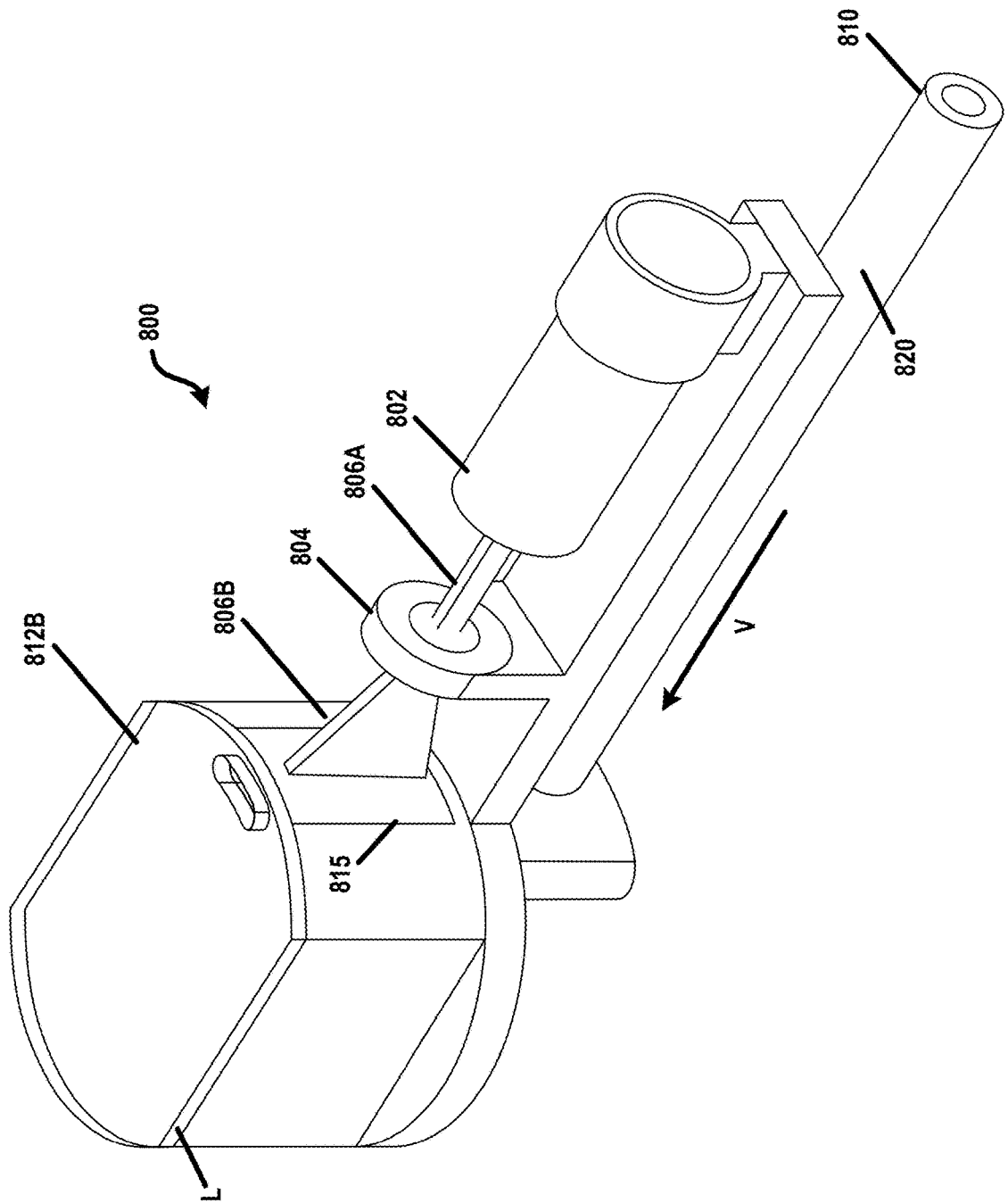
FIG. 12A is a diagram showing the vaporizer of FIG. 8, fully assembled and with a lid and a window installed in the reaction chamber.
Figure 12B:
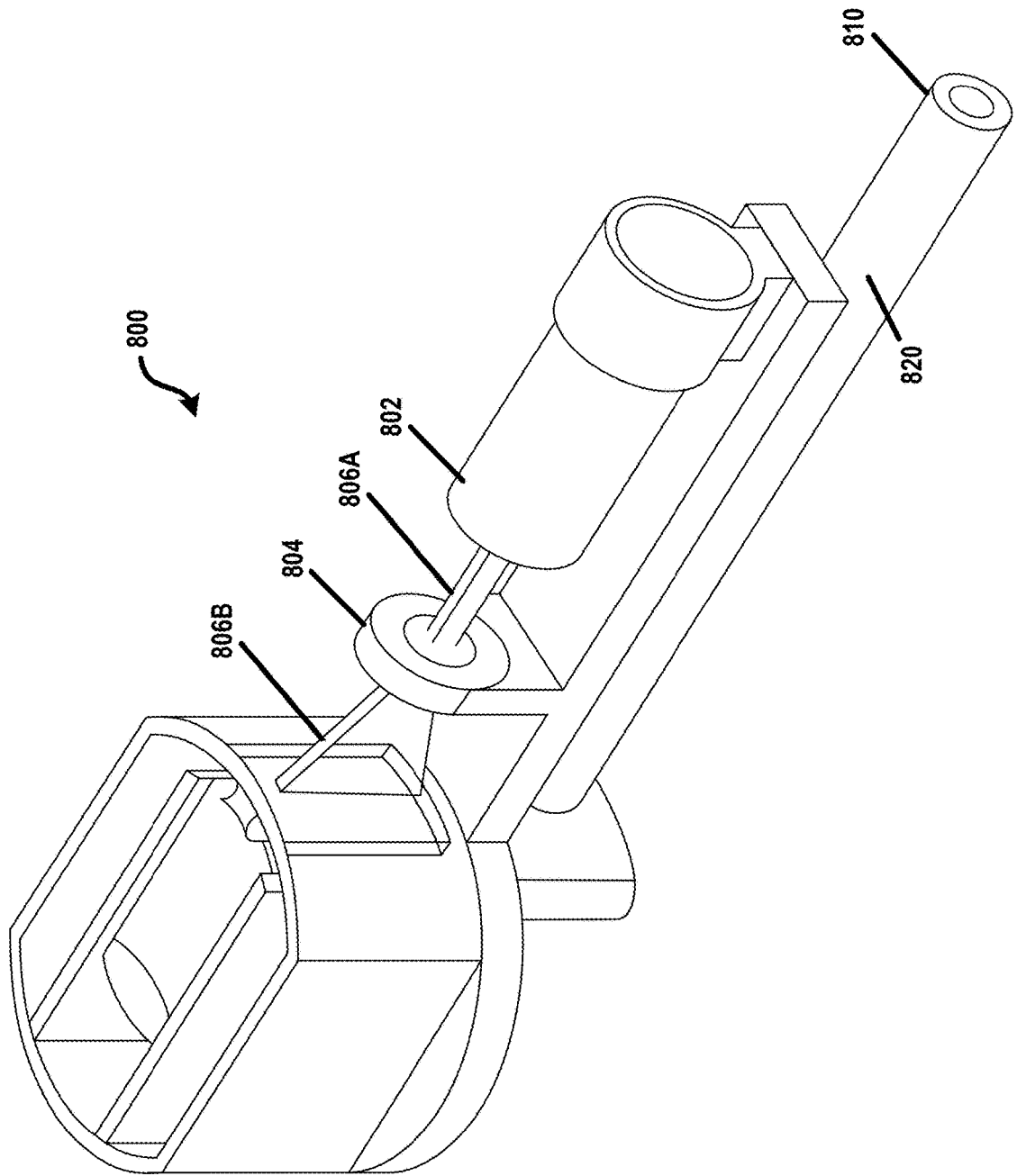
FIG. 12B is a diagram showing the vaporizer of FIG. 12A, with the lid removed.

FIGS. 9-11 are diagrams showing the vaporizer 800 of FIG. 8, fully assembled and with the reaction chamber 812A at different raster positions during operation. As shown in FIGS. 9-11, the assembled vaporizer 800 includes a reaction chamber housing 812B, with a body portion and a removable lid "L," the reaction chamber housing 812B having an opening 815 defined therein, through which the light 806B traverses during vaporization of the vaporization substance within the reaction chamber 812 during operation. In FIG. 9, the reaction chamber 812 (along with the other components of the reaction chamber assembly) has swiveled (i.e., moved about a rotational axis "R") to a leftmost position (when observed along a viewing line "V'), such that the light 806B impinges on a rightmost linear region of the opening 815, for example at a first time during operation. In FIG. 10, the reaction chamber 812 has swiveled to a rightmost position (when observed along a viewing line "V"), such that the light 806B impinges on a leftmost linear region of the opening 815, for example at a second time during operation. In FIG. 11, the reaction chamber 812 has swiveled to a central position (when observed along a viewing line "V"), such that the light 806B impinges on a central linear region of the opening 815, for example at a third time during operation. FIG. 12 is a diagram showing the vaporizer of FIG. 8, fully assembled and with a lid "L" and a window installed in the reaction chamber 812. FIG. 12B is a diagram showing the vaporizer of FIG. 12A, with the lid removed.

Although, in FIGS. 9-11, the reaction chamber (along with the other components of the reaction chamber assembly) is shown and described as swivelable about a rotational axis, in other embodiments, one or more of the laser source 802, the light 806A, the one or more lenses 804, or the light 806B is swivelable or rasterable (e.g., by motor-driven swiveling or translation of the laser source 802, the one or more lenses 804). Alternatively or in addition, the motorized mechanical agitator or scraper 813 and/or an additional agitator can be configured to swivel or translate the vaporization substance (e.g., a portion thereof) within the reaction chamber 812 to control a positioning of at least a portion of the vaporization substance relative to the light 806B. In some such implementations, the positioning of the at least a portion of the vaporization substance relative to the light 806B is more precise than in alternate embodiments, and as such, the opening 815 can be made smaller when the vaporization substance is positioned by the agitator(s).

Although, in FIGS. 9-11, the reaction chamber 812 is shown and described as including a lid "L," through which a vaporization substance can be replaced (i.e., in a reusable embodiment), in other embodiments, the vaporizer 800 is disposable (i.e., single-use) and the reaction chamber 812 has a one-piece/monolithic housing (i.e., no lid), such that the vaporization substance cannot be replaced.

Figure 13C:
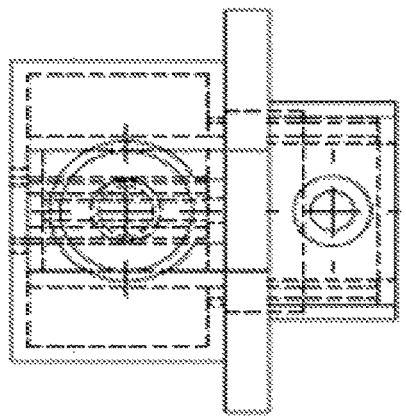
FIGS. 13A-13G are schematic renderings of a vaporizer similar to the vaporizer of FIG. 8, but with differences in component sizes, and showing internal structures thereof, according to some embodiments.
Figure 13B:
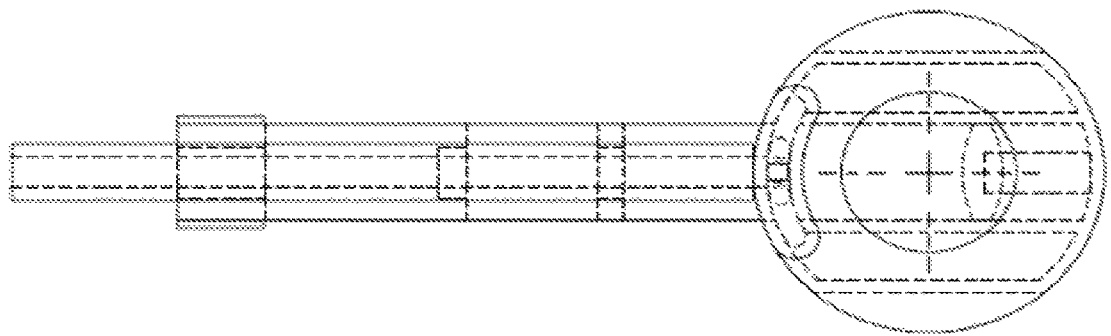
Figure 13A:
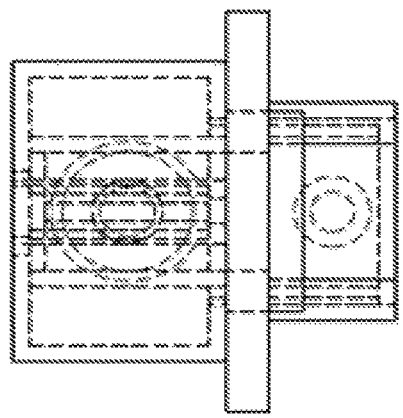
Figure 13D:
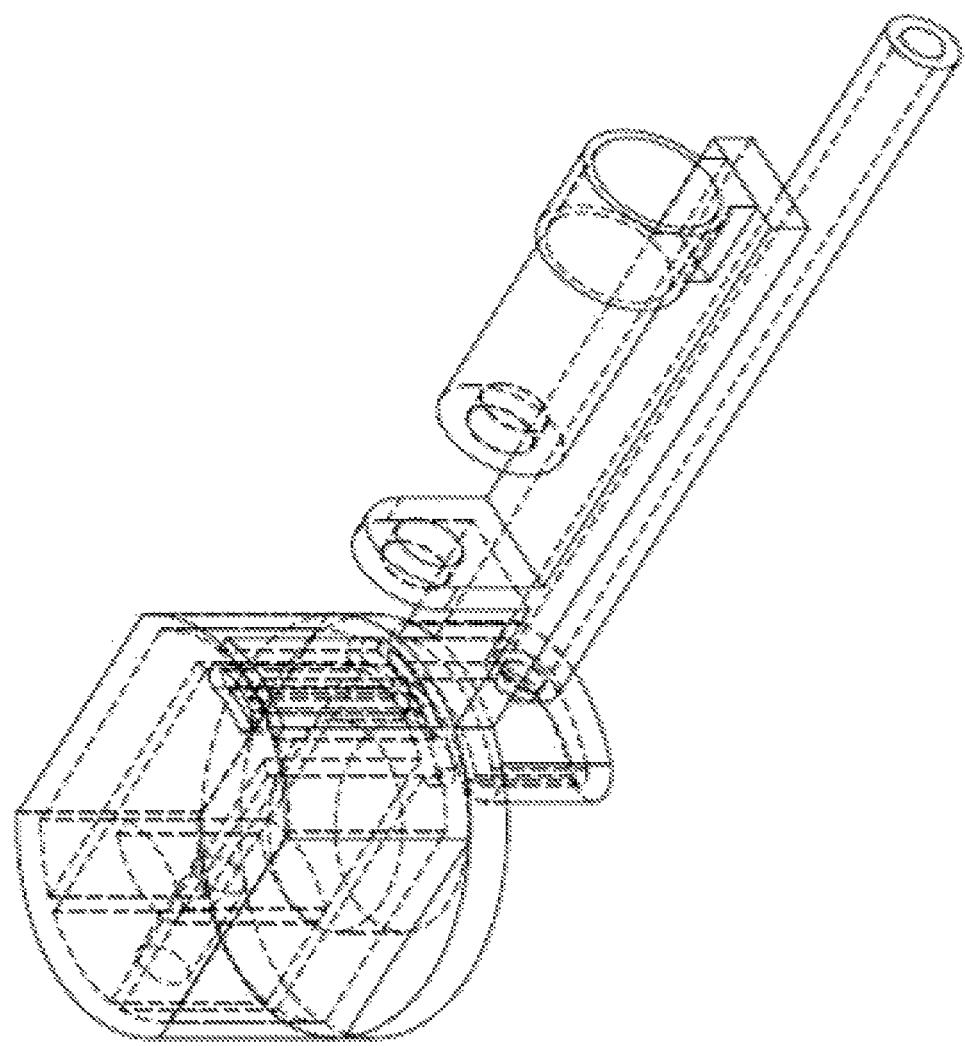
Figure 13G:
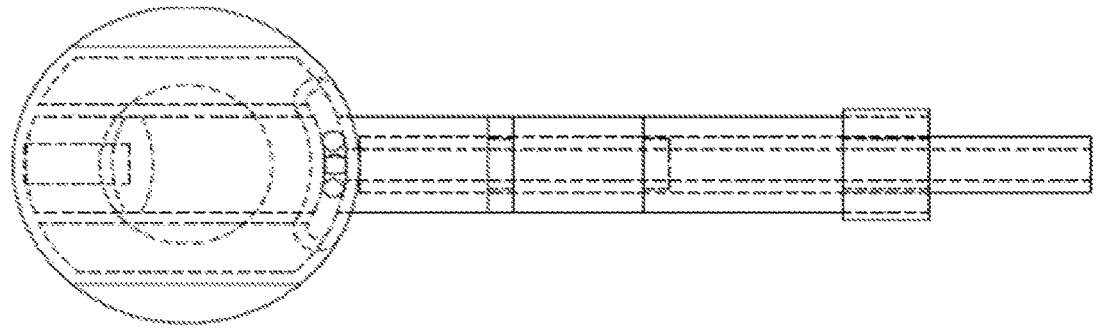
Figure 13E:
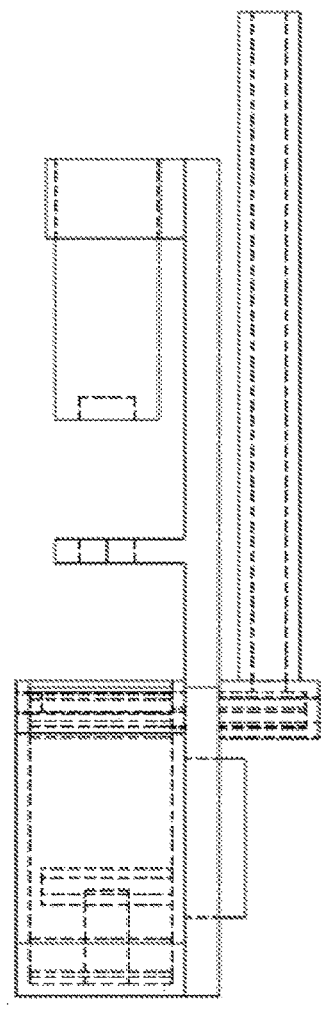
Figure 13F:
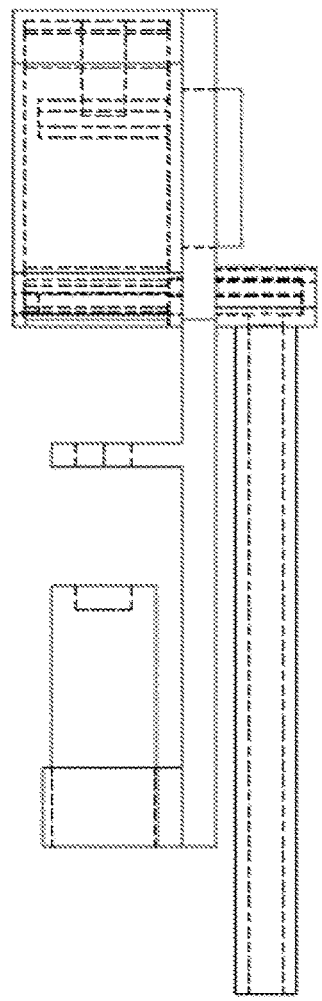

FIGS. 13A-13G are schematic renderings of a vaporizer similar to the vaporizer 800 of FIG. 8, but with differences in component sizes, and showing internal structures thereof, according to some embodiments. More specifically, FIG. 13A shows a rear/back view of the vaporizer 800, FIG. 13B shows a bottom view of the vaporizer 800, FIG. 13C shows a front view of the vaporizer 800, FIG. 13D shows an isometric view of the vaporizer 800, FIG. 13E shows a left side view of the vaporizer 800, FIG. 13F shows a right side view of the vaporizer 800, and FIG. 13G shows a top view of the vaporizer 800.

In some implementations, the laser heater assemblies shown and described with reference to FIGS. 2A through 13G are intended to be manufactured and sold as discrete modular components/units that are configured to be mechanically and electrically coupled to a vaporizer body (e.g., in the form of cartridges that can be inserted within or otherwise connected to a vaporizer housing). In other words, the laser heater assemblies can be sized and shaped for inclusion as a module within the vaporizer. In other implementations, the laser heater assemblies shown and described with reference to FIGS. 2A through 13G are intended to be incorporated into a vaporizer as part of the manufacturing process and prior to sale (e.g., for single-use/disposable vaporizers).

In some embodiments, an apparatus (e.g., a laser heater assembly) includes a power source, a laser source (e.g., a laser diode), a lens, and a reaction chamber. The laser source is electrically coupled to the power source and configured to emit light, the light propagating along an optical path during operation of the light source. The lens is disposed within the optical path (e.g., aligned with the laser source along the optical path). The reaction chamber is also disposed within the optical path (e.g., aligned with the laser source along the optical path), and includes an opening defined therein. The lens is configured to receive, during operation, emitted light from the laser source, and output a modified light having an energy profile that is substantially uniform (e.g., substantially uniform in space ("substantially spatially uniform") and/or in time ("substantially temporally uniform")). The laser source and the lens are configured such that, during operation, the modified light traverses at least a portion of the opening of the reaction chamber and vaporizes a vaporization substance (e.g., a dry plant material, optionally ground to a predefined size and/or density) disposed (e.g., received) within the reaction chamber. The light can be collimated light, and the modified light can be a homogeneous line profile beam. The homogeneous line profile beam can have a dimension that substantially matches, or has a predefined (e.g., a user-defined) proportional relationship (e.g., 1:1, 0.9:1, etc.) to, a dimension of the opening of the reaction chamber. For example, the homogeneous line profile beam can have a height that substantially matches a height of, or is a predetermined fraction of the height of, the opening of the reaction chamber. Alternatively or in addition, the homogeneous line profile beam can have a width that substantially matches a width of, or is a predetermined fraction of the width of, the opening of the reaction chamber. The lens can be a Powell lens configured to homogenize an energy field of the light. In some implementations, the laser source includes a Powell lens, and the light is collimated light.

In some embodiments, the apparatus also includes a swivel motor electrically coupled to the power source and mechanically coupled to the reaction chamber. The swivel motor is configured, during operation, to move the reaction chamber along a rotational path such that the vaporization substance is vaporized via a predefined portion of the opening of the reaction chamber.

In some embodiments, the apparatus also includes a swivel motor electrically coupled to the power source and mechanically coupled to the reaction chamber. The swivel motor is configured, during operation, to move the reaction chamber along a rotational path such that a portion of the vaporization substance is aligned with the opening of the reaction chamber.

In some embodiments, the apparatus also includes a processor and a swivel motor electrically coupled to the power source. The swivel motor is mechanically coupled to the reaction chamber. The processor is configured, during operation, to cause the swivel motor to move the reaction chamber along a rotational path such that the vaporization substance is vaporized via a predefined portion of the opening of the reaction chamber.

In some embodiments, the apparatus also includes a memory, a processor electrically coupled to the power source, an agitator electrically coupled to the power source, and a swivel motor electrically coupled to the power source. The memory stores instructions, executable by the processor, to cause the swivel motor to move the reaction chamber along a rotational path such that the vaporization substance is vaporized via a predefined portion of the opening of the reaction chamber. The memory also stores instructions, executable by the processor, to cause the agitator to move vaporized material to a receptacle of the reaction chamber. The memory also stores a representation of at least one of: a swivel speed, a swivel pattern, a swivel timing, a dwell time, an agitator speed, an agitator timing, or an agitator pattern.

In some embodiments, an apparatus (e.g., a vaporizer) includes a vapor tube including a mouthpiece, a power source, a laser source (e.g., a laser diode), a lens, and a reaction chamber. The laser source is electrically coupled to the power source and configured to emit light, the light propagating along an optical path during operation of the light source. The lens is disposed within (e.g., aligned with the laser source along) the optical path. The reaction chamber is also disposed within (e.g., aligned with the laser source along) the optical path and has an opening (e.g., a rectangular or rounded rectangular opening) defined therein. The vapor tube is fluidly coupled to (or in fluid communication with) at least a portion of the reaction chamber. The lens is configured to receive, during operation, emitted light from the laser source, and output a modified light having an energy profile that is substantially uniform (e.g., substantially uniform in space ("substantially spatially uniform") and/or in time ("substantially temporally uniform")). The laser source and the lens are configured such that, during operation, the modified light traverses at least a portion of the opening of the reaction chamber and vaporizes a vaporization substance (e.g., a dry plant material, optionally ground to a predefined size and/or density) disposed (e.g., received) within the reaction chamber. The light can be collimated light and the modified light can be a homogeneous line profile beam. The homogeneous line profile beam can have a dimension that substantially matches, or has a predefined (e.g., a user-defined) proportional relationship (e.g., 1:1, 0.9:1, etc.) to, a dimension of the opening of the reaction chamber. For example, the homogeneous line profile beam can have a height that substantially matches a height of, or is a predetermined fraction of the height of, the opening of the reaction chamber. Alternatively or in addition, the homogeneous line profile beam can have a width that substantially matches a width of, or is a predetermined fraction of the width of, the opening of the reaction chamber. The lens can be a Powell lens configured to homogenize an energy field of the light. In some implementations, the laser source includes a Powell lens and the light is collimated light.

In some embodiments, the apparatus also includes a swivel motor electrically coupled to the power source and mechanically coupled to the reaction chamber. The swivel motor is configured, during operation, to move the reaction chamber along a rotational path such that the vaporization substance is vaporized via a predefined portion of the opening of the reaction chamber.

In some embodiments, the apparatus also includes a swivel motor electrically coupled to the power source and mechanically coupled to the reaction chamber. The swivel motor is configured, during operation, to move the reaction chamber along a rotational path such that a portion of the vaporization substance is aligned with the opening of the reaction chamber.

In some embodiments, the apparatus also includes a processor and a swivel motor electrically coupled to the power source. The swivel motor is mechanically coupled to the reaction chamber. The processor is configured, during operation, to cause the swivel motor to move the reaction chamber along a rotational path such that the vaporization substance is vaporized via a predefined portion of the opening of the reaction chamber.

In some embodiments, the apparatus also includes a memory, a processor electrically coupled to the power source, an agitator electrically coupled to the power source, and a swivel motor electrically coupled to the power source. The memory stores instructions, executable by the processor, to cause the swivel motor to move the reaction chamber along a rotational path such that the vaporization substance is vaporized via a predefined portion of the opening of the reaction chamber. The memory also stores instructions, executable by the processor, to cause the agitator to move vaporized material to a receptacle of the reaction chamber. The memory also stores a representation of at least one of: a swivel speed, a swivel pattern, a swivel timing, a dwell time, an agitator speed, an agitator timing, or an agitator pattern.

In some embodiments, the apparatus also includes memory, a processor electrically coupled to the power source, and a pressure sensor electrically coupled to the power source. The pressure sensor can be configured to detect an inhalation, by a user, via the mouthpiece. The memory stores instructions, executable by the processor, to trigger the power source to supply power to the laser source in response to detecting the inhalation.

EXAMPLE EMBODIMENTS

In some embodiments, an apparatus includes an outer housing, a mouthpiece, a power source (e.g., a battery), and a laser diode assembly. The mouthpiece can be integral or mechanically attached to the outer housing, and is in fluid communication with a vapor tube. The power source is disposed within the housing. A recess is defined within the outer housing and configured to receive a vaporization substance. The vaporization substance includes a dry material, such as a plant material. The laser diode assembly includes a laser diode and a lens. The lens is configured to receive, during operation, light emitted from the laser diode, and to output a modified light having an energy profile that is substantially uniform. The apparatus is configured such that, during operation, the modified light vaporizes the vaporization substance.

In some embodiments, an apparatus includes a Powell lens, a laser diode, and an air chamber. The Powell lens is aligned with an optical path of the laser diode. The apparatus is sized and shaped for inclusion as a module within a vaporizer (e.g., sized and shaped to be mechanically attached to/mated with one or more other components of the vaporizer), and is configured, during operation, to receive a laser-generated light beam, and to emit light having a substantially uniform energy profile toward an outer surface of the air chamber to cause vaporization of a vaporization substance received within the air chamber.

In some embodiments, an apparatus includes at least one lens, a laser diode, and an agitator. The at least one lens is aligned with an optical path of the laser diode. The apparatus is sized and shaped for inclusion as a module within a vaporizer (e.g., sized and shaped to be mechanically attached to/mated with one or more other components of the vaporizer), and is configured, during operation, to receive a laser-generated light beam and to emit a substantially uniform line profile beam having an energy sufficient to induce vaporization of a vaporization substance.

In some embodiments, an apparatus includes a laser diode, a mirror galvanometer and an agitator. The mirror galvanometer is aligned with an optical path of the laser diode. The apparatus is sized and shaped for inclusion as a module within a vaporizer (e.g., sized and shaped to be mechanically attached to/mated with one or more other components of the vaporizer), and is configured, during operation, to receive a laser-generated light beam and to emit a substantially uniformly shaped light beam having an energy sufficient to induce vaporization of a vaporization substance.

In some embodiments, an apparatus includes a laser diode, a fiber optic array, and an agitator. The fiber optic array is at least partially aligned with an optical path of the laser diode. The apparatus is sized and shaped for inclusion as a module within a vaporizer (e.g., sized and shaped to be mechanically attached to/mated with one or more other components of the vaporizer), and is configured, during operation, to receive a laser-generated light beam and to emit a substantially uniformly shaped light beam having an energy sufficient to induce vaporization of a vaporization substance.

In some embodiments, an apparatus includes an outer housing, a mouthpiece, a power source disposed within the housing, a disc-shaped receptacle within the outer housing and configured to receive a vaporization substance, and a laser diode assembly. The laser diode assembly includes a laser diode and an optical diverter. The optical diverter is configured to reflect, during operation, light emitted from the laser diode toward the disc-shaped receptacle, such that the light causes vaporization of the vaporization substance when the vaporization substance is received in the disc-shaped receptacle. The apparatus can also be configured such that, during operation, the disc-shaped receptacle rotates and the light emitted from the laser diode rasters across a surface of the rotating disc-shaped receptacle to cause the vaporization of the vaporization substance.

All combinations of the foregoing concepts and additional concepts discussed herewithin (provided such concepts are not mutually inconsistent) are contemplated as being part of the subject matter disclosed herein. The terminology explicitly employed herein that also may appear in any disclosure incorporated by reference should be accorded a meaning most consistent with the particular concepts disclosed herein.

The skilled artisan will understand that the drawings primarily are for illustrative purposes, and are not intended to limit the scope of the subject matter described herein. The drawings are not necessarily to scale; in some instances, various aspects of the subject matter disclosed herein may be shown exaggerated or enlarged in the drawings to facilitate an understanding of different features. In the drawings, like reference characters generally refer to like features (e.g., functionally similar and/or structurally similar elements).

To address various issues and advance the art, the entirety of this application (including the Cover Page, Title, Headings, Background, Summary, Brief Description of the Drawings, Detailed Description, Embodiments, Abstract, Figures, Appendices, and otherwise) shows, by way of illustration, various embodiments in which the embodiments may be practiced. The advantages and features of the application are of a representative sample of embodiments only, and are not exhaustive and/or exclusive. Rather, they are presented to assist in understanding and teach the embodiments, and are not representative of all embodiments. As such, certain aspects of the disclosure have not been discussed herein. That alternate embodiments may not have been presented for a specific portion of the innovations or that further undescribed alternate embodiments may be available for a portion is not to be considered to exclude such alternate embodiments from the scope of the disclosure. It will be appreciated that many of those undescribed embodiments incorporate the same principles of the innovations and others are equivalent. Thus, it is to be understood that other embodiments may be utilized and functional, logical, operational, organizational, structural and/or topological modifications may be made without departing from the scope and/or spirit of the disclosure. As such, all examples and/or embodiments are deemed to be non-limiting throughout this disclosure.

Also, no inference should be drawn regarding those embodiments discussed herein relative to those not discussed herein other than it is as such for purposes of reducing space and repetition. For instance, it is to be understood that the logical and/or topological structure of any combination of any program components (a component collection), other components and/or any present feature sets as described in the figures and/or throughout are not limited to a fixed operating order and/or arrangement, but rather, any disclosed order is exemplary and all equivalents, regardless of order, are contemplated by the disclosure.

The term "automatically" is used herein to modify actions that occur without direct input or prompting by an external source such as a user. Automatically occurring actions can occur periodically, sporadically, in response to a detected event (e.g., a user logging in), or according to a predetermined schedule.

The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The term "processor" should be interpreted broadly to encompass a general purpose processor, a central processing unit (CPU), a microprocessor, a digital signal processor (DSP), a controller, a microcontroller, a state machine and so forth. Under some circumstances, a "processor" may refer to an application specific integrated circuit (ASIC), a programmable logic device (PLD), a field programmable gate array (FPGA), etc. The term "processor" may refer to a combination of processing devices, e.g., a combination of a DSP and a microprocessor, a plurality of microprocessors, one or more microprocessors in conjunction with a DSP core or any other such configuration.

The term "memory" should be interpreted broadly to encompass any electronic component capable of storing electronic information. The term memory may refer to various types of processor-readable media such as random access memory (RAM), read-only memory (ROM), non-volatile random access memory (NVRAM), programmable read-only memory (PROM), erasable programmable read only memory (EPROM), electrically erasable PROM (EEPROM), flash memory, magnetic or optical data storage, registers, etc. Memory is said to be in electronic communication with a processor if the processor can read information from and/or write information to the memory. Memory that is integral to a processor is in electronic communication with the processor.

The terms "instructions" and "code" should be interpreted broadly to include any type of computer-readable statement(s). For example, the terms "instructions" and "code" may refer to one or more programs, routines, subroutines, functions, procedures, etc. "Instructions" and "code" may comprise a single computer-readable statement or many computer-readable statements.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Some embodiments and/or methods described herein can be performed by software (executed on hardware), hardware, or a combination thereof. Hardware modules may include, for example, a general-purpose processor, a field programmable gate array (FPGA), and/or an application specific integrated circuit (ASIC). Software modules (executed on hardware) can be expressed in a variety of software languages (e.g., computer code), including C, C++, Java™, Ruby, Visual Basic™, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

Various concepts may be embodied as one or more methods, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments. Put differently, it is to be understood that such features may not necessarily be limited to a particular order of execution, but rather, any number of threads, processes, services, servers, and/or the like that may execute serially, asynchronously, concurrently, in parallel, simultaneously, synchronously, and/or the like in a manner consistent with the disclosure. As such, some of these features may be mutually contradictory, in that they cannot be simultaneously present in a single embodiment. Similarly, some features are applicable to one aspect of the innovations, and inapplicable to others.

In addition, the disclosure may include other innovations not presently described. Applicant reserves all rights in such innovations, including the right to embodiment such innovations, file additional applications, continuations, continuations-in-part, divisionals, and/or the like thereof. As such, it should be understood that advantages, embodiments, examples, functional, features, logical, operational, organizational, structural, topological, and/or other aspects of the disclosure are not to be considered limitations on the disclosure as defined by the embodiments or limitations on equivalents to the embodiments. Depending on the particular desires and/or characteristics of an individual and/or enterprise user, database configuration and/or relational model, data type, data transmission and/or network framework, syntax structure, and/or the like, various embodiments of the technology disclosed herein may be implemented in a manner that enables a great deal of flexibility and customization as described herein.

All definitions, as defined and used herein, should be understood to control over dictionary definitions, definitions in documents incorporated by reference, and/or ordinary meanings of the defined terms.

As used herein, in particular embodiments, the terms "about" or "approximately" when preceding a numerical value indicates the value plus or minus a range of 10%.

Where a range of values is provided, it is understood that each intervening value, to the tenth of the unit of the lower limit unless the context clearly dictates otherwise, between the upper and lower limit of that range and any other stated or intervening value in that stated range is encompassed within the disclosure. That the upper and lower limits of these smaller ranges can independently be included in the smaller ranges is also encompassed within the disclosure, subject to any specifically excluded limit in the stated range. Where the stated range includes one or both of the limits, ranges excluding either or both of those included limits are also included in the disclosure. As used herein, the term "substantially" has a meaning similar to "mostly" or "to a great extent." For example, the phrase "a substantially uniform thickness" refers to a thickness value plus or minus a range of 10%.

The indefinite articles "a" and "an," as used herein in the specification and in the embodiments, unless clearly indicated to the contrary, should be understood to mean "at least one."

The phrase "and/or," as used herein in the specification and in the embodiments, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the embodiments, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the embodiments, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the embodiments, shall have its ordinary meaning as used in the field of patent law.

As used herein in the specification and in the embodiments, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the embodiments, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

While specific embodiments of the present disclosure have been outlined above, many alternatives, modifications, and variations will be apparent to those skilled in the art. Accordingly, the embodiments set forth herein are intended to be illustrative, not limiting. Various changes may be made without departing from the spirit and scope of the disclosure.

The invention claimed is:

1. An apparatus, comprising:
   a power source;
   one or more laser sources electrically coupled to the power source and configured to emit light, the light propagating along an optical path during operation of the laser source;
   one or more lenses disposed within the optical path for converting a nominally collimated beam between the laser source and the one or more lenses into any of a substantially spatially uniform and a temporally uniform homogeneous line profile beam;
   a reaction chamber disposed within the optical path and having an opening defined therein; and
   a swivel motor electrically coupled to the power source and mechanically coupled to any of the one or more laser sources, one or more lenses, and the reaction chamber, the swivel motor configured, during operation, to move any of the one or more laser source, one or more lenses, and the reaction chamber along a rotational path such that the vaporization substance is vaporized via a predefined portion of the opening of the reaction chamber;
   wherein the homogeneous line profile beam has a dimension that substantially matches or has a predefined proportional relationship to a dimension of the opening of the reaction chamber; and
   wherein the one or more laser sources and the one or more lenses are configured such that, during operation, modified light traverses at least a portion of the opening of the reaction chamber and vaporizes a vaporization substance disposed within the reaction chamber.

2. An apparatus, comprising:
   a power source;
   one or more laser sources electrically coupled to the power source and configured to emit light, the light propagating along an optical path during operation of the laser source;
   one or more lenses disposed within the optical path for converting a nominally collimated beam between the laser source and the one or more lenses into any of a substantially spatially uniform and a temporally uniform homogeneous line profile beam;
a reaction chamber disposed within the optical path and having an opening defined therein;
a memory;
a processor electrically coupled to the power source;
an agitator electrically coupled to the power source; and
wherein the memory stores:
  instructions, executable by the processor, to cause the agitator to move vaporized material to a receptacle of the reaction chamber; and
  a representation of at least one of:
    a swivel speed,
    a swivel pattern,
    a swivel timing,
    a dwell time,
    an agitator speed,
    an agitator timing, or
an agitator pattern;
wherein the homogeneous line profile beam has a dimension that substantially matches or has a predefined proportional relationship to a dimension of the opening of the reaction chamber; and
wherein the one or more laser sources and the one or more lenses are configured such that, during operation, modified light traverses at least a portion of the opening of the reaction chamber and vaporizes a vaporization substance disposed within the reaction chamber.

3. The apparatus of claim 1, further comprising:
a vapor tube including a mouthpiece, the vapor tube fluidly coupled to at least a portion of the reaction chamber.

4. The apparatus of claim 1, further comprising;
a memory;
a processor electrically coupled to the power source; and
a pressure sensor electrically coupled to the power source;
wherein the pressure sensor is configured to detect an inhalation, by a user, via a mouthpiece, and
wherein the memory stores instructions, executable by the processor, to trigger the power source to supply power to the laser source in response to detecting the inhalation.

5. An apparatus, comprising:
a power source;
one or more laser sources electrically coupled to the power source and configured to emit light, the light propagating along an optical path during operation of the laser source;
one or more lenses disposed within the optical path for converting a nominally collimated beam between the laser source and the one or more lenses into any of a substantially spatially uniform and a temporally uniform homogeneous line profile beam;
a reaction chamber disposed within the optical path and having an opening defined therein; and
a plunger that, during operation, moves at least a portion of the vaporization substance within the reaction chamber;
wherein the homogeneous line profile beam has a dimension that substantially matches or has a predefined proportional relationship to a dimension of the opening of the reaction chamber; and
wherein the one or more laser sources and the one or more lenses are configured such that, during operation, modified light traverses at least a portion of the opening of the reaction chamber and vaporizes a vaporization substance disposed within the reaction chamber.

6. The apparatus of claim 2, further comprising:
a vapor tube including a mouthpiece, the vapor tube fluidly coupled to at least a portion of the reaction chamber.

7. The apparatus of claim 2, further comprising;
a memory;
a processor electrically coupled to the power source; and
a pressure sensor electrically coupled to the power source;
wherein the pressure sensor is configured to detect an inhalation, by a user, via a mouthpiece, and
wherein the memory stores instructions, executable by the processor, to trigger the power source to supply power to the laser source in response to detecting the inhalation.

8. The apparatus of claim 5, further comprising:
a vapor tube including a mouthpiece, the vapor tube fluidly coupled to at least a portion of the reaction chamber.

9. The apparatus of claim 5, further comprising;
a memory;
a processor electrically coupled to the power source; and
a pressure sensor electrically coupled to the power source;
wherein the pressure sensor is configured to detect an inhalation, by a user, via a mouthpiece, and
wherein the memory stores instructions, executable by the processor, to trigger the power source to supply power to the laser source in response to detecting the inhalation.

\* \* \* \* \*